(12) United States Patent
Shimizu et al.

(10) Patent No.: US 7,070,805 B2
(45) Date of Patent: Jul. 4, 2006

(54) RAPIDLY DISINTEGRABLE SOLID PREPARATION

(75) Inventors: Toshihiro Shimizu, Itami (JP); Masae Sugaya, Ikeda (JP); Yoshinori Nakano, Takarazuka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 09/800,839

(22) Filed: Mar. 7, 2001

(65) Prior Publication Data

US 2001/0010825 A1    Aug. 2, 2001

Related U.S. Application Data

(63) Continuation of application No. 09/403,429, filed as application No. PCT/JP99/04015 on Jul. 27, 1999.

(30) Foreign Application Priority Data

Jul. 28, 1998   (JP)   ................... 10-213049

(51) Int. Cl.
   *A61K 9/46*   (2006.01)
   *A61K 9/20*   (2006.01)
(52) U.S. Cl. ...................... 424/466; 424/464
(58) Field of Classification Search ............... 424/464, 424/465, 486, 488, 489, 466
   See application file for complete search history.

(56) References Cited

U.S. PATENT DOCUMENTS

| | | | |
|---|---|---|---|
| 4,371,516 A | 2/1983 | Gregory et al. | |
| 4,749,575 A | 6/1988 | Rotman | |
| 5,026,560 A | 6/1991 | Makino et al. | |
| 5,433,959 A | 7/1995 | Makino et al. | |
| 5,464,632 A | 11/1995 | Cousin et al. | |
| 5,501,861 A * | 3/1996 | Makino et al. | 424/464 |
| 5,549,911 A | 8/1996 | Leduc et al. | |
| 5,795,909 A * | 8/1998 | Shashoua et al. | 514/449 |
| 5,798,120 A | 8/1998 | Tomohisa et al. | |
| 5,824,339 A | 10/1998 | Shimizu et al. | |
| 5,855,914 A * | 1/1999 | Koyama et al. | 424/494 |
| 5,900,428 A | 5/1999 | Fandriks et al. | |
| 5,958,453 A * | 9/1999 | Ohno et al. | 424/465 |
| 6,132,770 A * | 10/2000 | Lundberg | 424/466 |
| 6,248,357 B1 | 6/2001 | Ohno et al. | |
| 6,287,596 B1 | 9/2001 | Murakami et al. | |
| 6,299,904 B1 * | 10/2001 | Shimizu et al. | 424/464 |
| 6,328,994 B1 | 12/2001 | Shimizu et al. | |
| 6,365,184 B1 | 4/2002 | Depui et al. | |
| 6,380,234 B1 | 4/2002 | Makino et al. | |
| 6,531,152 B1 | 3/2003 | Lerner et al. | |
| 6,586,004 B1 | 7/2003 | Shimizu et al. | |

FOREIGN PATENT DOCUMENTS

| | | |
|---|---|---|
| EP | 0 446 961 | 2/1987 |
| EP | 0 336 298 | 3/1989 |
| EP | 0 345 787 | 6/1989 |
| EP | 0 365 480 | 10/1989 |
| EP | 0 438 147 | 1/1991 |
| EP | 0 452 862 | 4/1991 |
| EP | 0 553 777 | 1/1993 |
| EP | 0 638 310 | 7/1994 |
| EP | 0 745 382 | 1/1995 |
| EP | 0 761 212 | 9/1996 |
| EP | 0 799 616 | 3/1997 |
| EP | 0 914 818 | 6/1997 |
| EP | 0 922 464 | 7/1997 |
| EP | 0 965 339 A1 | 11/1997 |
| EP | 0839526 A | 5/1998 |
| EP | 0 890 359 | 1/1999 |
| GB | 2 147 501 | 10/1984 |
| JP | 54-11226 | 1/1979 |
| JP | 12-68627 | 10/1989 |
| JP | 12-68628 | 10/1989 |
| JP | 4-066538 | 3/1992 |
| JP | 5-092918 | 4/1993 |
| JP | 5-310558 | 11/1993 |
| JP | 6-100601 | 4/1994 |
| JP | 6-305962 | 11/1994 |
| JP | 7-017853 | 1/1995 |
| JP | 8-027033 | 1/1996 |
| JP | 8-310969 | 11/1996 |
| JP | 09-048726 A | 2/1997 |
| JP | 9-71523 | 3/1997 |
| JP | 09-071523 A | 3/1997 |
| WO | WO 87/02240 | 4/1987 |
| WO | WO 92/11001 | 7/1992 |
| WO | WO 95/10264 | 4/1995 |
| WO | WO 96/01624 | 1/1996 |

(Continued)

OTHER PUBLICATIONS

Watanabe, Y., et.al., New Compressed Tablet Rapidly Disintegrating in Saliva in the Mouth using Crystalline . . . , *Biol. Pharm. Bull.* (1995), vol. 18, No. 9, pp. 1308-1310.

*Primary Examiner*—S. Tran
(74) *Attorney, Agent, or Firm*—Elaine M. Ramesh; Mark Chao

(57) ABSTRACT

A rapidly disintegrable solid preparation which comprises (i) a pharmacologically active ingredient, (ii) a sugar and (iii) a low-substituted hydroxypropylcellulose having 5% by weight or more to less than 7% by weight of hydroxypropoxyl group. The rapidly disintegrable solid preparation has fast disintegrability, suitable strength and no roughness.

2 Claims, No Drawings

FOREIGN PATENT DOCUMENTS

| WO | WO 96/24375 | 8/1996 |
| WO | WO 97/04728 | 2/1997 |
| WO | WO 97/25065 | 7/1997 |
| WO | WO 97/25066 | 7/1997 |
| WO | WO 97/25979 | 7/1997 |
| WO | WO 98/53798 | 12/1998 |
| WO | WO 99/59544 | 11/1999 |
| WO | WO 00/06126 | 2/2000 |

* cited by examiner

RAPIDLY DISINTEGRABLE SOLID PREPARATION

This application is a continuation of U.S. Patent Application Ser. No. 09/403,429, which was the National Phase filing of International Patent Application No. PCT/JP99/04015, filed Jul. 27, 1999.

TECHNICAL FIELD

The present invention relates to a solid preparation having fast disintegrability in the oral cavity with the existence of saliva, in a little water, or in the stomach particularly a rapidly disintegrable solid preparation which is useful as an orally disintegrable solid preparation.

BACKGROUND ART

It has been desired to develop an orally disintegrable solid preparation which can be easily administered to elders or children without water. As background arts which disclose such a preparation, for example, there are the following background arts.

JP-A-9-48726 discloses an orally rapidly disintegrable preparation produced by wetting in a moldable way on humidifying. It comprises a drug and a material which can retain the shape after molding and drying. As such materials, a sugar, sugar alcohol and a water-soluble polymer material are exemplified.

JP-A-9-71523 discloses a tablet containing a drug, crystalline cellulose, a low-substituted hydroxypropylcellulose and a lubricant. It has fast disintegrability in the oral cavity.

EP-A839526 discloses a solid pharmaceutical preparation containing a pharmacologically active ingredient, erythritol, crystalline cellulose and a disintegrator.

However, these background arts have not described (i) a pharmacologically active ingredient, (ii) a sugar and (iii) a low-substituted hydroxypropylcellulose having 5% by weight or more to less than 7% by weight of hydroxypropoxyl group of the present invention.

DISCLOSURE OF INVENTION

There has been desired the development of a rapidly disintegrable solid preparation having fast disintegrability in the existence of saliva in the oral cavity, in a little water or in the stomach, having suitable strength (hardness) so that it may not be damaged through production processes and distribution, and further having no roughness.

The present invention relates to:

(1) a rapidly disintegrable solid preparation which comprises (i) a pharmacologically active ingredient, (ii) a sugar and (iii) a low-substituted hydroxypropylcellulose having 5% by weight or more to less than 7% by weight of hydroxypropoxyl group;

(2) the preparation of the above (1), which is an orally rapidly disintegrable solid preparation;

(3) the preparation of the above (1) or (2), which is a tablet;

(4) the preparation of the above (1), wherein the sugar is a sugar alcohol;

(5) the preparation of the above (4), wherein the sugar alcohol is mannitol or erythritol;

(6) the preparation of the above (1), wherein the sugar is comprised in an amount of 5 to 97 parts by weight per 100 parts by weight of the solid preparation;

(7) the preparation of the above (1), wherein the low-substituted hydroxypropylcellulose having 5% by weight or more to less than 7% weight of hydroxypropoxyl group is used in an amount of 3 to 50 parts by weight per 100 parts by weight of the solid preparation;

(8) the preparation of the above (1), wherein the pharmacologically active ingredient is lansoprazole;

(9) the preparation of the above (1), wherein the pharmacologically active ingredient is voglibose;

(10) the preparation of the above (1), wherein the pharmacologically active ingredient is manidipine hydrochloride;

(11) the preparation of the above (1), wherein the pharmacologically active ingredient is pioglitazone hydrochloride;

(12) the preparation of the above (1), wherein the pharmacologically active ingredient is candesartan cilexetil;

(13) the preparation of the above (3) which comprises fine granules;

(14) the preparation of the above (13), wherein the pharmacologically active ingredient is comprised in the fine granules.

(15) the preparation of the above (14), wherein (i) a sugar and (ii) a low-substituted hydroxypropylcellulose having 5% by weight or more to less than 7% by weight of hydroxypropoxyl group are comprised in the solid preparation separately from the fine granules;

(16) the preparation of the above (15), wherein the sugar is in an amount of 5 to 97 parts by weight per 100 parts by weight of the rest of the solid preparation other than the fine granules;

(17) the preparation of the above (15), wherein the low-substituted hydroxypropylcellulose having 5% by weight or more to less than 7% by weight of hydroxypropoxyl group is in an amount of 3 to 50 parts by weight per 100 parts by weight of the rest of the solid preparation other than the fine granules;

(18) use of a low-substituted hydroxypropylcellulose having 5% by weight or more to less than 7% by weight of hydroxypropoxyl group for producing a rapidly disintegrable solid preparation comprising a pharmacologically active ingredient and a sugar; and

(19) a method for improving fast disintegrability of a solid preparation comprising a pharmacologically active ingredient and a sugar, which is characterized in that a low-substituted hydroxypropylcellulose having 5% by weight or more to less than 7% by weight of hydroxypropoxyl group is contained therein.

1)Pharmacologically Active Ingredient

The pharmacologically active ingredients used in the present invention are in any condition such as solid, powdery, crystalline, oily and solution conditions. As such pharmacologically active ingredients, for example, one or more ingredient(s) selected from the group comprising nourishing and cordial agents, antipyretic-anodyne-anti-inflammatory drugs, psychotropics, antianxiety drugs, antidepressants, hypnotic-sedative drugs, spasmolytics central nervous system drugs, brain metabolism ameliorating agents, brain circulation ameliorating agents, antiepileptics, sympathomimetics, gastrointestinal agents, antacids, antiulcer agents, antitussive-expectorants, antiemetics, respiratory accelerators, bronchodilators, antiallergic drugs, dental buccal drugs, antihistamines, cardiotonics, antiarrythmic drugs, diuretics, antihypertensive agents, vasoconstrictors, coronary vasodilators, peripheral vasodilators, antihypolipidemic agents, cholagogues, antibiotics, chemotherapeutic drugs, antidiabetic agents, drugs for osteoporosis, antirheumatism agents, skeletal muscle relaxants, antivertigos, hormones, alkaloid narcotics, sulfa drugs, arthrifuges, blood coagulation inhibitors, antitumor agents, drugs for Alzheimer's disease and the like are exemplified.

As the nourishing and cordial agents, for instance, vitamins such as vitamin A, vitamin D, vitamin E (such as d-α-tocopherol acetate and the like), vitamin $B_1$ (such as dibenzoylthiamine, fursultiamine hydrochloride and the like), vitamin $B_2$ (such as riboflavin butyrate and the like), vitamin $B_6$ (such as pyridoxine hydrochloride and the like), vitamin C (such as ascorbic acid, sodium L-ascorbate and the like) and vitamin $B_{12}$ (such as hydroxocobalamin acetate, cyanocobalamin and the like); minerals such as calcium, magnesium, iron and the like; proteins, amino acids, oligosaccharides, crude drugs and the like are exemplified.

As the antipyretic-anodyne-antiinflammatory drugs, for instance, aspirin, acetaminophen, ethenzamide, ibuprofen, diphenhydramine hydrochloride, dl-chlorpheniramine maleate, dihydrocodeine phosphate, noscapine, methylephendrine hydrochloride, phenylpropanolamine hydrochloride, caffeine, anhydrous caffein, serrapeptase, lysozyme chloride, tolfenamic acid, mefenamic acid, sodium diclofenac, flufenamic acid, salicylamide, aminopyrine, ketoprofen, indomeacin, bucolome, pentazocine and the like are exemplified.

As the antipsychotics, for instance, chlorpromazine, reserpine and the like are exemplified.

As the antianxiety drugs, for instance alprazolam, chlordiazepoxide, diazepam and the like are exemplified.

As the antidepressants, for instance, imipramine, maprotiline hydrochloride, amphetamine and the like are exemplified.

As the hypnotic-sedative drugs, for instance, estazolam, nitrazepam, diazepam, perlapine, sodium phenobarbital and the like are exemplified.

As the spasmolytics, for instance, scopolamine hydrobromide, diphenhydramine hydrochloride, papaverine hydrochloride and the like are exemplified.

As the central nervous system drugs, for instance, citicoline and the like are exemplified.

As the brain metabolism ameliorating agents, for instance, meclofenoxate hydrochloride and the like are exemplified.

As the brain circulation ameliorating agents, for instance, vinpocetine and the like are exemplified.

As the antiepileptics, for instance, phenytoin, carbamazepine and the like are exemplified.

As the sympathomimetics, for instance, isoproterenol hydrochloride and the like are exemplified.

As the gastroinetestinal agents, for instance, stomachic-digestives such as diastase, saccharated pepsin, scopolia extract, cellulase AP3, lipase AP and cinnamon oil; agents for intestinal disorders such as berberine chloride, resistant lactic acid bacterium, Lactobacillus bifidus and the like are exemplified.

As the antacids, for instance, magnesium carbonate, sodium hydrogen-carbonate, magnesium aluminometasilicate, synthetic hydrotalcite, precipitated calcium carbonate, magnesium oxide and the like are exemplified.

As the antiulcer agents, for instance, lansoprazole, omerprazole, rabeprazole, pantoprazole, famotidine, cimetidine, rantidine hydrochloride and the like are exemplified.

As the antitussive expectorants, for instance, chloperastine, hydrochloride, dextromethorphan hydrobromide, theophylline, potassium guaiacolsulfonate, guaiafenesin, codeine phosphate and the like are exemplified.

As the antiemetics, for instance, difenidol hydrochloride, metoclopramide and the like are exemplified.

As the respiratory accelerators, for instance, levallorphan tartrate and the like are exemplified.

As the bronchodilators, for instance, theophylline, salbutanol sulfate and the like are exemplified.

As the antiallergic drugs, for instance, amlexanox, seratrodast and the like are exemplified.

As the dental buccal drugs, for instance, oxyltetracycline, triamicinolone acetonide, chlorhexidine hydrochloride, lidocaine and the like are exemplified.

As the antihistamines, for instance, diphenhydramine hydrochloride, promethazine, isothipendyl hydrochloride, dl-chlorpheniramine maleate and the like are exemplified.

As the cariotinics, for instance, caffeine, digoxin and the like are exemplified.

As the antiarrythmic drugs, for instance, procainamide hydrochloride, propranolol hydrochloride, pindolol and the like are exemplified.

As the diuretics, for instance, isosorbide, furosemide, thiazides such as HCTZ and the like are exemplified.

As the antihypertensive agents, for instance, delapril hydrochloride, captopril, hexamethonium bromide, hydrazine hydrochloride, labetalol hydrochloride, manidipine hydrochloride, candesartan, cilexetil, methyldopa, losartan, valsartan, eprosartan, irbesartan, tasosartan, telmisartan, and the like are exemplified.

As the vasoconstrictors, for instance, phenylephrine hydrochloride and the like are exemplified.

As the coronary vasodilators, for-instance, carbocromen hydrochloride, molsidomine, verapamil hydrochloride and the like are exemplified.

As the peripheral vasodilators, for instance, cinnarizine and the like are exemplified.

As the antihypolipidemic agents, for instance, sodium cerivastatin, simvastatin, sodium pravastatin and the like are exemplified.

As the cholagogues, for instance, dehydrocholic acid, trepibutone and the like are exemplified.

As the antibiotics, for instance, cephems such as cefalexin, cefaclor, amoxicillin, pivmecillinam hydrochloride, cefotiam hexetyl hydrochloride, cefadroxil, cefixime, cefditoren pivoxil, cefteram pivoxyl, cefpodoxime proxetil, cefotiam dihydrochloride, cefozopran hydrochloride, cefmenoxime hemihydrochloride, sodium cefsulodin; synthetic antibacterial agents such as ampicillin, ciclacillin, sodium sulbenicillin, nalidixic acid and enoxacin; monobactams such as sodium carumonam; penems; carbapenems and the like are exemplified.

As the chemotherapeutic drugs, for instance, sulfamethizole, sulfamethizole hydrochloride, thiazosulfone and the like are exemplified.

As the antidiabetic agents, for instance, tolbutamide, voglibose, pioglitazone hydrochloride, glibenclamide, troglitazone, rosiglitazone maleate, acarbose, miglitol, emigitate and the like are emeplified.

As the drugs for osteoporosis, for instance, ipriflavone and the like are exemplified.

As the skeletal muscle relaxants, for instance, methocarbamol and the like are exemplified.

As the antivertigos, for instance, meclizine hydrochloride, dimenhydrinate and the like are exemplified.

As the antirheumatism agents, for instance, methotrexate, bucillamine, and the like are exemplified.

As the hormones, for instance, sodium liothyronine, dexamethasone sodium phosphate, prednisolone, oxendolone, leuprorelin acetate and the like are exemplified.

As the alkaloid narcotics, for instance, opium, morphine hydrochloride, ipecac, oxycodone hydrochloride, opium alkaloids hydrochlorides, cocaine hydrochloride and the like are exemplified.

As the sulfa drugs, for instance, sulfamine, sulfisomidine, sulfamethizole and the like are exemplified.

As the arthrifuges, for instance, allopurinol, colchicine and the like are exemplified.

As the blood coagulation inhibitors, for instance, dicourmarol and the like are exemplified.

As the antitumor agents, for instance, 5-fluorouracil, uracil, mitomycin and the like are exemplified.

As the drugs for Alzheimer's disease, for instance, idebenone, vinpocetine and the like are exemplified.

Among the above pharmacologically active ingredients, nourishing and cordial agents, antipyretic-anodyne-anti-inflammatory drugs, hypnotic-sedative drugs, central nervous system drugs, gastrointestinal agents, antiulcer agents, antitussive-expectorants, antiallergic drugs, antiarrythmic drugs, diuretics, antihypertensive agents, vasoconstrictors, coronary vasodilators, antihypolipidemic agents, antidiabetic agents, drugs for osteoporosis, skeltal muscle relaxants, antivertigos and the like are exemplified.

In the present invention, the pharmacologically active ingredients preferably used are antiulcer agents such as lansoprazole; antidiabetic agents such as voglibose and pioglitazone hydrochloride; and antihypertensive agents such as manidipine hydrochloride and candesartan cilexetil and the like are exemplified.

Two or more pharmacologically active ingredients can be optionally used in an admixture in a rapidly disintegrable solid preparation of this invention.

The pharmacologically active ingredient is optionally diluted by the diluents generally used in the fields of medical treatment and food. In addition, it is optionally treated for the purpose of masking the bitterness of the pharmacologically active ingredient.

The above pharmacologically active ingredient is used in an amount of, for example, 0.01 to 70 parts by weight, preferably 0.02 to 50 parts by weight, more preferably 0.05 to 30 parts by weight, per 100 parts by weight of the solid preparation.

2) Sugar

As the sugars used in the present invention, for example, sugar, starch sugar, lactose, honey and sugar alcohol are exemplified. Such sugars are optionally used in an admixture thereof with suitable ratio.

As the sugar, for example, sucrose, coupling sugar, fructooligosaccharide, palatinose are exemplified.

As the starch sugar, for example, glucose, maltose, powdered sugar, starch syrup, fructose and fruit sugar and the like are exemplified.

As the lactose, for example, lactose, isomerized lactose (lactulose), reduced lactose (lactitol) and the like are exemplified.

As the honey, various kinds of honey which are generally edible are exemplified.

As the sugar alcohol, for example, sorbitol, mannitol, maltitol, reduced starch saccharide, xylitol, reduced paratinose, erythritol, and the like are exemplified. As erythritol is optionally one used which is produced by fermentation using glucose as a starting material with yeast in general and has at most 50 mesh of the particle size. Such erythritol is commercially available [for example, from Nikken Chemicals Co., Ltd, (Japan)].

The above sugars are preferably water-soluble sugars. The water-soluble sugars mean any water-soluble sugars which need at most 30 ml of water when 1 g of sugar is added into water and then dissolved within 30 minutes at 20° C. strongly shaking every 5 minutes for 30 seconds.

In the present invention, the sugar is preferably the sugar alcohol, more preferably mannitol or erythritol.

In order to obtain sufficient strength of the preparation and sufficiently fast disintegrability, the sugar is used in an amount of 5 to 97 parts by weight, preferably 10 to 90 parts by weight, per 100 parts by weight of the solid preparation in case of the solid preparation not comprising fine granules. On the other hand, the sugar is used in an amount of 5 to 97 parts by weight, preferably 10 to 90 parts by weight, per 100 parts by weight of the rest of the solid preparation other than the fine granules in case of the solid preparation comprising fine granules.

For example, mannitol or erythritol is usually used in an amount of 5 to 90 weight %, preferably 10 to 80 weight %, more preferably 20 to 80 weight %, especially preferably 50 to 80 weight % relative to the whole solid preparation in case of the solid preparation not comprising fine granules. On the other hand, mannitol or erythritol is usually used in an amount of 5 to 90 weight %, preferably 10 to 80 weight %, more preferably 20 to 80 weight %, especially preferably 50 to 80 weight % relative to the rest of the solid preparation other than the fine granules in case of the solid preparation comprising fine granules.

3) Low-Substituted Hydroxypropylcellulose Having 5% By Weight or More to Less Than 7% By Weight of Hydroxypropoxyl Group (L-HPC)

3-1) Production of L-HPC

The "low-substituted hydroxypropylcellulose having 5% by weight or more to less than 7% by weight of hydroxypropoxyl group (hereinafter, optionally referred to L-HPC)" used in the present invention can be produced in accordance with well-known methods, for example, methods described in JP-B-57-53100 or its analogous methods thereof.

At fist, alkaline cellulose containing free alkaline and propylene oxide are reacted to obtain the crude low-substituted hydroxypropylcellulose containing free alkaline.

Concretely, for example, raw material pulp such as wood pulp and cotton linter is immersed in 10 to 50% concentration of an aqueous solution of sodium hydroxide, and pressed to obtain the alkaline cellulose of which NaOH/cellulose ratio is 0.1 to 1.2 (ratio by weight). Next, the crude low-substituted hydroxypropylcellulose containing free alkaline is obtained by reacting the resulting alkaline cellulose and propylene oxide with stirring at 20 to 90° C. for 2 to 8 hours. Propylene oxide is used in an amount so that the content of hydroxypropoxyl group in the desired low-substituted hydroxypropylcellulose can be 5% or more by weight to less than 7% by weight.

The crude low-substituted hydroxypropylcellulose containing free alkaline is dispersed in water or hot water containing 5 to 80% of acid which is necessary to neutralize the total amount of alkaline, and a part of the crude low-substituted hydroxypropylcellulose containing free alkaline is dissolved therein. Further, acid is added to neutralize the remaining alkaline.

After the neutralization, processes such as drainage, drying and grinding are performed in accordance with the conventional method to obtain the desired low-substituted hydroxypropylcellulose.

3-2) Property of L-HPC

The particle diameter of L-HPC used in the present invention is, for example, 5 to 60 μm as average particle diameter. Preferably, it is 10 to 40 μm as average particle diameter.

In the above ranges, in case that L-HPC having relatively large particle diameter (for example, L-HPC having 26 to 40 μm of average particle diameter) is used, a pharmaceutical preparation being superior in disintegrability can be produced. On the other hand, in case that L-HPC having relatively small particle diameter (for example, L-HPC having 10 to 25 μm of average particle diameter) is used, the pharmaceutical preparation being superior in strength of the preparation can be produced.

Accordingly, the particle diameter of L-HPC can be suitably selected according to the character of the desired pharmaceutical preparation.

In order to obtain sufficient strength of the preparation and sufficiently fast disintegrability, the L-HPC in the present invention is used in an amount of 3 to 50 parts by weight, preferably 5 to 40 parts by weight, per 100 parts by weight of the solid preparation in case of the solid preparation not comprising fine granules. On the other hand, the L-HPC in the present invention is used in an amount of 3 to 50 parts by weight, preferably 5 to 40 parts by weight, per 100 parts by weight of the rest of the solid preparation other than the fine granules in case of the solid preparation comprising fine granules.

As mentioned above, by using L-HPC, it becomes possible to improve fast disintegrability, particularly the orally fast disintegrability, of the solid preparation containing the pharmacologically active ingredient and the sugar.

4) Dosage Forms

As the dosage form of the rapidly disintegrable solid preparation of the present invention, for example, tablet, granule, fine granule and the like, preferably tablet is exemplified. Among rapidly disintegrable tablets such as an orally disintegrable tablet and a tablet disintegrable in water, the orally disintegrable tablet is preferable.

5) Other Ingredients

Unless fast disintegrability (particularly, fast disintegrability in the oral cavity) or strength of the preparation is interfered with, the rapidly disintegrable solid preparation of the present invention may further contain a variety of additives which are commonly used in the manufacture of preparations in general dosage forms. Amount of such additives to be used is one commonly used in the manufacture of preparations in general dosage forms. As such additives, for example, binders, acids, foaming agents, artificial sweeteners, flavorants, lubricants, colorants, stabilizers, excipients, disintegrators and the like are exemplified.

As the above binders, for example, hydroxypropylcellulose, hydroxypropylmethylcellulose, crystalline cellulose, pregelatinized starch, polyvinylpyrrolidone, gum arabic powder, gelatin, pullulan and the like are exemplified. These two or more binders can be used in an admixture in a given ratio. The use of crystalline cellulose as the binder provides the solid preparation which exhibits more excellent strength of the preparation while retaining excellent fast disintegrability in the oral cavity. As the crystalline cellulose, microcrystalline cellulose is also included. The "crystalline cellulose" includes a refined one having partially α-cellulose depolymerization. As crystalline cellulose, for example, CEOLUS KG 801, Avicel PH 101, Avicel PH 102, Avicel PH 301, Avicel PH 302, Avicel RC-A591 NF (crystalline cellulose ·carmellose sodium), Avicel RC-591 (crystalline cellulose·carmellose sodium)and the like are concretely exemplified. Among them, CEOLUS KG 801 referred to as highly moldable crystalline cellulose is preferably used. Such crystalline celluloses are optionally used in an admixture thereof with suitable ratio. Such crystalline celluloses can be commercially available (manufactured by Asahi Chemical Industry Co., Ltd. (Japan)). The crystalline cellulose is used in an amount of, for example, 1 to 50 parts by weight, preferably 2 to 40 parts by weight, more preferably 2 to 20 parts by weight, per 100 parts by weight of the solid preparation in case of the solid preparation not comprising fine granules. Likewise, the crystalline cellulose is used in an amount of, for example, 1 to 50 parts by weight, preferably 2 to 40 parts by weight, more preferably 2 to 20 parts by weight, per 100 parts by weight of the solid preparation apart from fine granules in case of the solid preparation comprising fine granules.

As the acids, for example, citric acid, tartaric acid, malic acid and the like are exemplified.

As the foaming agents, for example, sodium bicarbonate and the like are exemplified.

As the artificial sweeteners, for example, saccharin sodium, dipotassium glycyrrhizinate, aspartame, stevia, thaumatin and the like are exemplified.

As the flavorants, for example, lemon, lemon lime, orange, menthol, strawberry and the like are exemplified.

As the lubricants, for example, magnesium stearate, sucrose fatty acid ester, polyethylene glycol, talc, stearic acid and the like are exemplified. Use of polyethylene glycol as the lubricant provides the stable-solid preparation of which the decomposition over time of the pharmacologically active ingredient is controlled. At that time, polyethylene glycol is used in an amount of, for example, 0.01 to 10 parts by weight, preferably 0.1 to 5 parts by weight, per 100 parts by weight of the solid preparation in case of the solid preparation not comprising fine granules. Likewise, polyethylene glycol is used in an amount of, for example, 0.01 to 10 parts by weight, preferably 0.1 to 5 parts by weight, per 100 parts by weight of the solid preparation apart from fine granules in case of the solid preparation comprising fine granules.

As the colorants, for example, various food colorants such as Food Yellow No. 5, Food Red No.2, Food Blue No. 2 and the like; food lakes, red iron oxide and the like are exemplified.

As the stabilizers, for example, a basic substance in the case of the basic pharmacologically active ingredient and an acidic substance in the case of the acidic pharmacologically active ingredient are exemplified.

As the excipients, for example, lactose, sucrose, D-mannitol, starch, corn starch, crystalline cellulose, light silicic anhydride, titanium oxide and the like are exemplified.

As the disintegrators, for example, disintegrators called super disintegrators such as crospovidone [manufactured by ISP Inc. (U.S.A.), BASF (Germany)], croscarmellose sodium [FMS-Asahi Chemical Industry Co., Ltd. (Japan)], carmellose calcium ]Gotoku Chemical (Yakuhin), (Japan)]; hydroxypropylcellulose; low-substituted hydroxypropylcellulose; carboxymethylstarch sodium [Matsutani Chemical Co., Ltd. (Japan)]; corn starch and the like are exemplified. Among them, crospovidone is preferably used. Such two or more disintegrators are optionally used in an admixture thereof with suitable ratio.

As crospovidone, any cross-lined homopolymer such as 1-ethenyl-2-pyrrolidinone homopolymer may be used, and usually crospovidone having a molecular weight of at least 1,000,000 is used. As crospovidone which is commercially available, for example, Cross-linked povidone, Kollidone CL [manufactured by BASF (Germany)], Polyplasdone XL, Polyplasdone XL-10, INF-10 [manufactured by ISP Inc., (U.S.A.)], polyvinylpolypyrrolidone, PVPP, 1-vinyl-2-pyrrolidinone homopolymer and the like are concretely exemplified.

Two or more of these disintegrants can be as a mixture in a given ratio. For example, (i) crospovidone solely, or (ii) crospovidone and another disintegrant(s) is preferably used.

Such disintegrator is used in an amount of, for example, 0.1 to 20 parts by weight, preferably 1 to 10 parts by weight, more preferably 3 to 7 parts by weight, per 100 parts by weight of the solid preparation in case of the solid preparation not comprising fine granules. Likewise, such disintegrator is used in an amount of, for example, 0.1 to 20 parts by weight, preferably 1 to 10 parts by weight, more preferably 3 to 7 parts by weight, per 100 parts by weight of the rest of the solid preparation other than the fine granules in case of the solid preparation comprising fine granules.

5-1) Other Ingredients for Dosage Forms, especially of Acid-labile Pharmacologically Active Ingredient In case that the pharmacologically active ingredient is an acid-labile one such as lansoprazole, omeprazole, rapeprazole, pantoprazole and the like, a basic inorganic salt is preferably incorporated to stabilize the pharmacologically active ingredient in the solid preparation.

The "basic inorganic salt" includes, for example, a basic inorganic salt of sodium potassium magnesium and/or calcium, preferably a basic inorganic salt of magnesium and/or calcium. Among others, preferred is a basic inorganic salt of magnesium.

The basic inorganic salt of sodium includes, for example, sodium carbonate, sodium hydrogencarbonate, sodium phosphate, sodium hydrogenphosphate and the like.

The basic inorganic salt of potassium includes, for example, potassium carbonate, potassium hydrogencarbonate, potassium phosphate, potassium hydrogenphosphate, potassium sodium carbonate and the like.

The basic inorganic salt of magnesium includes, for example, heavy magnesium carbonate, magnesium carbonate, magnesium oxide, magnesium hydroxide, magnesium metasilicate aluminate, magnesium silicate aluminate, magnesium silicate, magnesium aluminate, synthetic hydrotalcite [$Mg_6Al_2(OH)_{16} \cdot CO_3 \cdot 4H_2O$], aluminum magnesium hydroxide [$2.5MgO \cdot Al_2O_3 \cdot xH_2O$] and the like. Among others, preferred is heavy magnesium carbonate, magnesium carbonate, magnesium oxide, magnesium hydroxide and the like.

The basic inorganic salt of calcium includes, for example, precipitated calcium carbonate, calcium hydroxide, and the like.

The preferable examples of the "basic inorganic salt" are magnesium basic inorganic salt, and more preferable examples include heavy magnesium carbonate, magnesium carbonate, magnesium oxide, magnesium hydroxide, and the like.

Such basic inorganic salt of magnesium or calcium, and the like has a basic pH (not less than 7) when it is in the form of a 1% aqueous solution or suspension.

Two or more of these basic inorganic salts (preferably a basic inorganic salt of magnesium, a basic inorganic salt of calcium, and the like) can be used as a mixture in a given ratio. The amount of the basic inorganic salt to be used is appropriately selected depending on the kind of the basic inorganic salt and is, for instance, 0.3 to 200 parts by weight, preferably 1 to 100 parts by weight, more preferably 10 to 50 parts by weight, especially preferably 20 to 40 parts by weight relative to the pharmacologically active ingredient.

6) Dosage Form containing Fine Granules (e.g., Tablet)

As was mentioned before, the rapidly disintegrable preparation of the present invention can be used in any solid dosage form such as tablet, granule, fine granule and the like. In case that it is a tablet, the tablet can contain fine granules. The fine granules may contain the pharmacologically active ingredient. These dosage forms can be prepared by a conventional method or its analogous method.

7) Fine Granules containing Core

The fine granule can contain a core together with or separately from the pharmacologically active ingredient. As such a core, for example, (1) a spherical granulated product comprising crystalline cellulose and lactose [e.g., a spherical granulated product being 100 to 200 μm and comprising crystalline cellulose (3 parts) and lactose (7 parts) (Nonpareil 105 (trade name), manufactured by Freund Industrial Co., Ltd. (Japan)), a spherical granulated product being 150 to 250 μm and comprising crystalline cellulose (3 parts) and lactose (7 parts) (Nonpareil NP-7:3 (trade name), manufactured by Freund Industrial Co., Ltd. (Japan), a spherical granulated product being 150 to 250 μm and comprising crystalline cellulose (5 parts) and lactose (5 parts) (Nonpareil NP-5:5 (trade name), manufactured by Freund Industrial Co., Ltd. (Japan)) and the like], (2) a spherical granulated product being 150 to 250 μm and comprising crystalline cellulose [avicel SP (trade name), manufactured by Asahi Chemical Industry Co., Ltd. (Japan) and the like) and the like are exemplified.

In case that a core is used, the core is optionally coated with the pharmacologically active ingredient and the like, and further coated for masking taste or smell and/or for imparting enteric dissolubility or sustained-release property by well known methods. In this case, such a core forms a fine granule comprising the pharmacologically active ingredient. As a coating agent in this case, for example, enteric-coated polymers (e.g., cellulose acetate phthalate (CAP), methacrylate copolymer L, methacrylate copolymer LD (Eudragit L30D-55(trade name; manufactured by Rohm GmbH (Germany))), methacrylate copolymer S, hydroxypropylmethylcellulose phthalate, hydroxymethylcellulose acetate succinate, hydroxypropylmethylcellulose acetate succinate, KolIICoat MAE30DP (trade name; manufactured by BASF (Germany)), Polyquid PA-30 (trade name; manufactured by SanyoKasei (Japan)), carboxymethylethylcellulose, shellac, methacrylate copolymer [e.g., Eudragit NE30D (trade name), Eudragit RL30D (trade name), Eudragit RS30D (trade name), and the like] triethyl citrate, polyethylene glycol, acetylated monoglyceride, triacetin, castor oil, and the like), gastric dissolvable polymers (e.g., polyvinylacetal diethylaminoacetate, aminoalkyl methacrylate copolymer and the like), water-soluble polymers (e.g., hydroxypropylcellulose, hydroxypropylmethylcellulose and the like), slightly soluble-polymers (e.g., ethylcellulose, aminoalkyl methacrylate copolymer RS, ethyl acrylate methyl methacrylate copolymer and the like), wax and the like are exemplified. One or more kind(s) of coating agents are used in an admixture.

7-1) Production of Fine Granules

The "fine granules" in the present invention can be produced by a known granulation method.

The "granulation method" includes, for example, rolling granulation method (e.g., centrifugal rolling granulation, etc.), fluidized-bed granulation (e.g., rolling fluidized-bed granulation, fluidized granulation, etc.), stirring granulation and the like. Among others, preferred is fluidized-bed granulation method, more preferred is rolling fluidized-bed granulation method.

Concrete example of the "rolling granulation method" includes a method using "CF apparatus" manufactured by Freund Industrial Co., Ltd. (Japan) and the like. Concrete examples of the "rolling fluidized-bed granulation method" include methods using "SPIR-A-FLOW", "multi plex" manufactured by Powrex Corp. (Japan), "New-Marumerizer" manufactured by Fuji Paudal Co., Ltd. (Japan), and the like. The method for spraying the mixture can be suitably selected in accordance with the kind of granulator, and may be, for example, any one of a top spray method, a bottom spray method, a tangential spray method, and the like. Among others, a tangential spray method is preferred.

The "fine granules" in the present invention can be coated with any other ingredient including the active ingredient and the others, by a conventional coating method or its analogous method. For example, a method which comprises coating a core comprising crystalline cellulose and lactose with an acid-liable physiologically active substance is employed in case that pharmacologically active ingredient is an acid-liable physiologically active substance.

For example, used is a method described in JP-A-5-92918 (coating method), which comprises coating a core comprising crystalline cellulose and lactose with an acid-labile physiologically active substance, if necessary together with a basic inorganic salt, binders, lubricants, excipients, a water-soluble polymer, etc. (hereinafter, may be abbreviated to "coating layer"). For example, employed is a method which comprises coating a core with an acid-labile physiologically active substance and a basic inorganic salt, and then further with binders, lubricants, excipients, a water-soluble polymer, etc.

7-2) Property of Core for Fine Granules

The average particle diameter of the "cores" is 250 µm or less, preferably 50 to 250 µm, more preferably 100 to 250 µm, especially preferably 100 to 200 µm. The "cores" having the above average particle diameter include particles which all pass through a #50 sieve (300 µm), particles where 5 w/w % or less of the total remain on a #60 sieve (250 µm), and particles where 10 w/w % or less of the total pass through a #282 sieve (53 µm). The specific volume of the "core" is 5 ml/g or less, preferably 3 ml/g or less.

Examples of the "core" include:

(1) a spherical granulated product comprising crystalline cellulose and lactose, (2) a spherical granulated product being 150 to 250 µm and comprising crystalline cellulose (Avicel SP, manufactured by Asahi Chemical Co., Ltd. (Japan)), (3) a stirring granulated product being 50 to 250 µm and comprising lactose (9 parts) and a starch (1 part), (4) a micro particle being 250 µm or less classified as a spherical granule comprising micro crystalline cellulose described in JP-A-61-213201, (5) a processed product such as wax formed to a sphere by spraying or melting granulation, (6) a processed product such as gelatin beads comprising oil component, (7) calcium silicate, (8) starch, (9) a porous particle such as chitin, cellulose, chitosan, etc, and (10) a bulk product such as granulated sugar, crystalline lactose or sodium chloride, and processed preparations thereof. Further, these cores may be produced in accordance with per se known grinding method or granulation method, and sifted to prepare the particles having the desired particle diameter.

The above "spherical granulated product comprising crystalline cellulose and lactose" includes, for example (i) a spherical granulated product being 100 to 200 µm and comprising crystalline cellulose (3 parts) and lactose (7 parts) [e.g., Nonpareil 105 (70–140) (particle diameter of 100 to 200 µm), manufactured by Freund Industrial Co., Ltd. (Japan)], (ii) a spherical granulated product being 150 to 250 µm and comprising crystalline cellulose (3 parts) and lactose (7 parts) [e.g., Nonpareil NP-7:3, manufactured by Freund Industrial Co., Ltd. (Japan)], (iii) a spherical granulated product being 100 to 200 µm and comprising crystalline cellulose (4.5 parts) and lactose (5.5 parts) [e.g., Nonpareil 105T (70–140) (particle diameter of 100 to 200 µm), manufactured by Freund Industrial Co., Ltd. (Japan)], (iv) a spherical granulated product being 150 to 250 µm and comprising crystalline cellulose (5 parts) and lactose (5 parts) [e.g., Nonpareil NP-5:5, manufactured by Freund Industrial Co., Ltd. (Japan)], and the like.

In order to produce a pharmaceutical preparation which is superior in dissolution while retaining suitable strength, the "core" includes, for example, preferably the spherical granulated product comprising crystalline cellulose and lactose, more preferably the spherical granulated material comprising crystalline cellulose and lactose and containing 50 weight % or more of lactose relative to the whole solid preparation. Among others, preferred is a core comprising 40 to 50 weight % of crystalline cellulose and 50 to 60 weight % of lactose.

As the "core" employed in the present invention, preferably, there may be employed the spherical granulated product comprising crystalline cellulose and lactose, more preferably the spherical granulated product with a diameter of 100 to 200 µm and comprising crystalline cellulose (4.5 parts) and lactose (5.5 parts).

The "core" may contain the physiologically active substance such as the above described pharmacologically active ingredient. Also, the "core" may not contain the physiologically active substance because the release of the physiologically active substance can be controlled by a coating layer containing the physiologically active substance.

The "core" is preferably as uniform a sphere as possible, for reducing the irregularity of the coating, in addition to being a powdery core.

The ratio of the "coating layer" to the "core" can be selected within the range in which it is possible to control dissolution of the physiologically active substance and particle size of the composition, for example, usually 50 to 400 parts weight relative to 100 parts by weight of the core.

7-3) Coating Method of Fine Granules

The coating layer may be constructed by plural layers. At least one layer of the plural layers must contain the physiologically active substance. The combination of various layers such as a coating layer not containing the active ingredient, a base coating layer, and an enteric coating layer which constitute the coating layer can be suitably selected.

In case that the "core" is coated, for example, the above physiologically active substance and the water-soluble polymer can be employed in an admixture thereof. The admixture may be a solution or a dispersion, and can be prepared by using an organic solvent such as water or ethanol or an admixture thereof.

The concentration of the water-soluble polymer in the admixture varies according to the ratio of the physiologically active substance and the additives, and is usually 0.1 to 50 weight %, preferably 0.5 to 10 weight % relative to the whole solid preparation, in order to retain the binding strength of the physiologically active substance to the core and maintain the viscosity of the mixture so as not to reduce the workability.

Where the coating layer comprises plural layers, the concentration of the physiologically active substance in each layer may be changed successively or gradually by selecting for the content ratio or viscosity of the water-soluble polymer or by successive coating with mixtures varying in the ratio of the physiologically active substance and the other additives. In the above case, it may be coated with a mixture in which the content ratio of the water-soluble polymer is out of the range of 0.1 to 50 weight %, as long as the coating layer as a whole contains 0.1 to 50 weight % of the water-soluble polymer. Further, in forming the inactive coat according to known methods, the coating layer optionally comprises some layers such that the inactive layer may block each layer containing the physiologically active substance.

Also, in case of two or more physiologically active substances not suited in the compatibility, the core may be coated by employing each mixture together or separately.

The above coated material is dried, and passed through sieves to obtain a "composition" having uniform size. Because the form of the composition is usually according to the core, a fine granule being in the form of a rough sphere can be obtained. As the sieve may be employed, for example a #50 circular sieve (300 μm). The composition is obtained by selecting those which pass through the #50 circular sieve.

The "fine granule" in the present invention can be produced in accordance with in the same manner as above granulation method, for example, a method which comprises coating the composition with an enteric coating layer, in order to protect the physiologically active substance or to impart enteric dissolution. If necessary, the composition coated with an enteric coating layer may be further coated by a water-soluble sugar alcohol, preferably mannitol. In such case, the strength of the orally disintegrable tablet comprising fine granules is improved.

The "enteric coating layer" is preferably a layer having 20 to 70 μm, preferably 30 to 50 μm of thickness and coating the whole surface of the composition containing the physiologically active substance. Accordingly, the smaller particle diameter of the composition, the higher the weight % of the enteric coating layer in the whole fine granule. In the fine granule of the present invention, the "enteric coating layer" is 30 to 70 weight %, preferably 50 to 70 weight %, of the fine granule as a whole.

The "enteric coating layer" are optionally constructed by plural (e.g., 2 or 3) layers. For example, the used is a method which comprises coating a composition with an enteric coating layer having polyethyleneglycol, and then with an enteric coating layer having triethyl citrate, followed by being coated with an enteric coating layer having polyethyleneglycol.

8) Production of Rapidly Disintegrable Solid Preparation

The rapidly disintegrable solid preparation of the present invention can be produced in accordance with a conventional method or its analogous method in the field of pharmaceutical preparation. As such method, for example, a method comprising blending the pharmacologically active ingredient, the sugar and the low-substituted hydroxypropylcellulose having 5% by weight or more to less than 7% by weight of hydroxypropoxyl group after adding water if needed, molding, and then drying if needed is exemplified. However, the rapidly disintegrable solid preparation of the present invention can be produced also without water.

8-1) Production of Rapidly Disintegrable Tablet

For the production of the orally disintegrable tablet, a conventional molding method or its analogous method can be applied by using appropriate ingredients selected from the above-mentioned ones including the fine granules.

Preferred example of the method for the orally disintegrable tablet having the fine granules of the coated cores comprises:

(i) coating a core comprising crystalline cellulose and lactose with a physiologically active substance and an excipient, followed by being coated with a coating layer comprising a water-soluble polymer to obtain a composition, (ii) coating the resultant composition with an enteric coating layer having polyethyleneglycol, and then with an enteric coating layer having triethyl citrate, and then followed by being coated by mannitol to obtain fine granule, and (iii) blending the resultant fine granule with an additive, followed by molding.

The molding procedure can be carried out, for instance, by tableting with a pressure of 0.5 to 3 ton/cm$^2$, preferably 1 to 2ton/cm$^2$ by using a single-punch tabletting machine [Kikusui Seisakusho (Japan)] or a rotary type tabletting machine [Kikusui Seisakusho (Japan)] when a solid preparation is a tablet, especially an orally disintegrable tablet.

The drying procedure can be carried out by any techniques such as vacuum drying, fluidized-bed drying and the like used to dry the general pharmaceutical preparation.

The blending procedure can be carried out by any conventional blending techniques such as admixing, kneading, granulating and the like. The blending procedure is carried out by using an apparatus such as Vertical Granulator VG10 [manufactured by Powrex Corp. (Japan)], Universal Kneader [manufactured by Hata Iron Works Co., Ltd. (Japan)], fluidized bed granulator LAB-1 and FD-3S [manufactured by Powrex Corp. (Japan)], centrifugal fluidized coating granulator MP-10, MP-400 [manufactured by Powrex Corp. (Japan)] and the like.

In the present specification, "coating" means also partial coating and adhesion or adsorption in addition to coating the whole surface of an object (e.g., core) which is to be coated.

"Spherical" means also forms having a curved surface such as forms having elliptic cross sections, and forms in the shapes of eggplants and drops in addition to spheres.

"Average particle diameter" means volume based distribution median diameter (median diameter: 50% particle diameter from cumulative distribution), unless otherwise specified. It can be measured by, for example, a laser diffraction particle distribution measurement method. Concretely exemplified is a method using Raiser Diffraction Analyzer, type: HEROS RODOS [trade name; manufactured by Sympatec (Germany)].

In the present invention, "fine granules" have an average particle diameter of about 400 μm or less, in order that roughness is not felt in the mouth. Preferably, the average particle diameter of the fine granules is 300 to 400 mm.

Aside from the average particle diameter of the above "fine granules", regarding the maximum particle size, the particle diameter is substantially 428 μm or less, and preferably substantially 400 μm or less. Preferably, the particle diameter is substantially 300 to 425 μm, more preferably 300 to 400 μm.

"Substantially" as used in the phases of "the particle diameter is substantially 425 μm or less" and "the particle diameter is substantially 400 μm or less" means that the particles may include a small quantity (about 5 weight % or less) of particles whose particle diameter is out of the above described range, to include the inevitable contaminant particles.

The "composition" may contain water-soluble polymers, the above binders, lubricants, excipients and the like in common use as pharmaceutical materials. The amount of such water-soluble polymers, binders, lubricants, and excipients is selected from amounts commonly employed in the manufacture of preparations in general dosage forms.

The "water-soluble polymer" includes, for example, a water-soluble polymer which is soluble in ethanol (i.e., an ethanol-soluble water-soluble polymer) such as a cellulose derivative (e.g., hydroxypropyl cellulose, which may be referred to as "HPC" hereinafter), polyvinylpyrrolidone, etc.; a water-soluble polymer which is insoluble in ethanol (i.e., an ethanol-insoluble water-soluble polymer) such as a cellulose derivative (e.g., hydroxypropylmethyl cellulose, which may be referred to as "HPMC" hereinafter, methyl cellulose, carboxymethyl cellulose sodium, etc.), sodium polyacrylate, polyvinyl alcohol, sodium alginate, and guar gum, etc.

When such water-soluble polymers are used, the dissolution of drugs (physiologically active substances) can be controlled by employing them in combination with the ethanol-soluble water-soluble polymer and ethanol-insoluble water-soluble polymer or by employing them in combination with some water-soluble polymers having different viscosity.

In the present invention, the "water-soluble polymer" is preferably, a cellulose derivative such as HPC, HPMC, and methyl cellulose, and polyvinyl alcohol. More preferred is a cellulose derivative such as HPC, HPMC.

The "HPC" contains, for example, about 53.4 to 77.5 weight %, more preferably about 60 to 70 weight %, of hydroxypropoxyl group. The viscosity of 2 weight % aqueous solution of HPC at 20° C. is usually about 1 to 1500,000 cps (centipose). As the above HPC, hydroxypropyl cellulose defined in Japanese Pharmacopoeia may be employed. Hereinafter, all viscosity of HPC is a value of 2 weight % aqueous solution at 20° C.

The "HPC" is a mixed ether which is connected by a methoxy group and a hydroxypropoxy group. The content of the methoxy group of HPMC is, for example, about 19 to 30 weight %. The content of the hydroxypropoxy group is, for example, about 4 to 12 weight %. The viscosity of 2 weight % aqueous solution of HPMC at 20° C. is usually about 1 to 40,000 centistokes. As such HPMC may be employed hydroxypropylmethyl cellulose 2208 defined by Japanese Pharmacopoeia, hydroxypropylmethyl cellulose 2906 defined by Japanese Pharmacopoeia, hydroxypropylmethyl cellulose 2910 defined by Japanese Pharmacopoeia, and so forth. Hydroxypropyl cellulose(s) may be employed alone or in an admixture of two or more thereof.

The content of the water-soluble polymer such as HPC and/or HPMC is usually about 0.1 to 50 weight %, preferably about 1 to 30 weight %, as against the whole "composition" containing the physiologically active substance, in order to control the dissolution of the physiologically active substance in the composition containing the physiologically active substance and retain a high content of the physiologically active substance.

In the present invention, the "fine granules" may contain, for example, titanium oxide as a masking agent.

The diameter of the "orally disintegrable tablet" of the present invention is about 5 to 20 mm, preferably about 7 to 15 mm, more preferably about 8 to 13 mm.

The "orally disintegrable tablet" optionally may not comprise lubricant inside the tablet.

When the "fine granule" of the present invention is used for a tablet except for an orally disintegrable tablet, the diameter of the tablet is about 5 to 10 mm, preferably about 5 to 8 mm. When the fine granule of the present invention is used for a capsule, the size of the capsule is preferably a #2 capsule or less.

9) Property of Rapidly Disintegrable Solid Preparation

The rapidly disintegrable solid preparation of the present invention thus obtained exhibits fast disintegrability or dissolubility in the oral cavity, water or stomach, and suitable strength of the preparation. Further the rapidly disintegrable solid preparation of the present invention is improved in chalky taste and has no roughness.

9-1) Disintegration Time

The oral disintegration time of the rapidly disintegrable solid preparation of the present invention (the time for healthy male or female adults to complete disintegration by buccal saliva) is usually 5 to 50 seconds, preferably 5 to 40 seconds, more preferably 5 to 35 seconds.

The disintegration time in the stomach of the rapidly disintegrable solid preparation of the present invention (the time for healthy male or female adults to complete disintegration) is shorter than that of the normal preparation such as a normal tablet.

The disintegration time of the rapidly disintegrable solid preparation of the present invention in water is usually 5 to 40 seconds, preferably 5 to 30 seconds, more preferably 5 to 25 seconds.

9-2) Strength of Preparation

The strength of the rapidly disintegrable solid preparation of the present invention (measurement with a tablet hardness tester) is usually 2 to 20 kg, preferably 4 to 15 kg.

9-3) Administration Manner

The rapidly disintegrable solid preparation of the invention is especially used for an orally disintegrable tablet and can be administered without water or together with water.

As administration methods, there are listed (1) a method of administration by dissolution or disintegration together with a little water, or without water and with saliva in the oral cavity, not to be swallowed as it is, or (2) a method of administration with water, where it is swallowed as it is. Also, the tablet may be administered dissolved or disintegrated with water.

The "orally disintegrable tablet" of the present invention is advantageously used in (a) cases where administration without water is necessary, (b) cases of administration to a patients who have difficulty in swallowing tablets, or (c) cases of administration to the aged or to children where there is a fear of blocking the throat if it is in usual tablet form.

The rapidly disintegrable solid preparation of the present invention can be safely administered orally to mammals such as mouse, rat, rabbit, cat, dog, bovine, horse, monkey, human and the like.

9-4) Dose and Specific Embodiments

While the dosage amount of the rapidly disintegrable solid preparation varies depending on a pharmacologically active ingredient, a subject, a kind of disease and the like, the dosage amount is selected so that the dosage amount of the pharmacologically active ingredient can be an effective amount.

In case of the above (a), the orally disintegrable tablet is preferably used for antipyretic agents, analgesic agents, anti-inflammatory agents, antianxiety drugs, antitussive-expectorants, anti motion sickness agents, drugs for prevention and treatment for car-sickness, and the like.

In case of the above (b), the orally disintegrable tablet is preferably used for preventing and/or treating hypertension, hyperlipemia, diabetes, bronchial asthma, cerebrovascular diseases, and the like.

9-4-1) Lansoprazole

For instance, when lansoprazole is used as the pharmacologically active ingredient, the rapidly disintegrable solid preparation of the present invention is useful for treatment and prevention of digestive ulcer (such as gastric ulcer, duodenal ulcer, anastomic ulcer, Zollinger-Ellison syndrome), gastritis, reflex esophagitis and the like; eradication of H. pylori; suppression of upper gastrointestinal bleeding caused by digestive ulcer, acute stress ulcer and hemorrhagic gastritis; suppression of upper gastrointestinal bleeding caused by invasive stress (such as stress caused by a large-scale operation necessitating the following intensive management or cerebrovascular disease, head injury, failure to many organs, burn injury of a wide range which necessitate intensive care); treatment and prevention of ulcer caused by non-steroidal anti-inflammatory agent; treatment and prevention of gastric hyperacidity and ulcer caused by postoperative stress; administration before anesthesia and the like. The dosage amount of the preparation per an adult (body weight: 60 kg) is 0.5 to 1500 mg/day, preferably 5 to 150 mg/day, as lansoprazole.

9-4-2) Voglibose

When voglibose is used as the pharmacologically active ingredient, the rapidly disintegrable solid preparation of the present invention is useful for treatment and prevention of obesity, adiposis, lipemia, diabetes mellitus and the like. The dosage amount of the preparation per an adult (body weight: 60 kg) is 0.01 to 30 mg/day, preferably 0.1 to 3 mg/day, as voglibose. The rapidly disintegrable solid preparation can be administered once a day, or 2 to 3 times separately a day.

9-4-3) Manidipine·HCl

When manidipine hydrochloride is used as the pharmacologically active ingredient, the rapidly disintegrable solid preparation of the present invention is useful for treatment and prevention of circulatory system diseases such as hypertension, ischemic heart disease (e.g. angina pectoris, myocardial infarction and the like), cerebral and peripheral circulatory disorders (e.g., cerebral infarction, transient ischemic attack, constriction of renal artery and the like) and the like. The dosage amount of the preparation per an adult (body weight: 60 kg) is 1 is 200 mg/day, preferably 10 to 20 mg/day, as manidipine hydrocyloride. The rapidly disintegrable solid preparation is usually administered once a day after breakfast.

9-4-4) Pioglitazone·HCl

When pioglitazone hydrochloride is used as the pharmacologically active ingredient, the rapidly disintegrable solid preparation of the present invention is useful as the insulin resistance improving agent the like, and for treatment and prevention of diabetes mellitus. The dosage amount of the preparation per an adult (body weight: 60 kg) is 7.5 to 60 mg/day, preferably 15 to 45 mg/day, as pioglitazone hydrochloride. The rapidly disintegrable solid preparation can be administered once a day, or 2 to 3 times separately a day.

9-4-5) Candesartan Cilexetil

Further, when candesartan cilexetil is used as the pharmacologically active ingredient, the rapidly disintegrable solid preparation of the present invention is useful for treatment and prevention of hypertension, heart diseases, cerebral applexy, renal diseases and the like. The dosage amount of the preparation per an adult (body weight: 60 kg) is 1 to 50 mg/day, preferably 2 to 30 mg/day, as candesartan cilexetil.

BEST MODE FOR CARRYING OUT THE INVENTION

The present invention is more specifically explained by means of the following Reference Examples, Examples and Test Examples. It is to be understood that the present invention is not limited to these Examples.

Unless otherwise specifically indicated, the following "%" mean % by weight.

Also, the content of hydroxypropoxyl group is measured in accordance with the methods described in Japanese Pharamcopoeia (e.g., 13th edition). The physical properties (hardness and disintegration time) of the tablets were determined by the following test methods.

(1) Hardness Test

Determination was carried out with a tablet hardness tester [manufactured by Toyana Sangyo Co. Ltd. (Japan)]. The test was performed in 10 runs and mean values were shown.

(2) Oral Disintegration Time

Time for complete disintegration or dissolution of the tablets only by saliva in the oral cavity was determined.

EXAMPLES

Reference Example 1

An alkaline cellulose comprising 24.1% of NaOH, 1.7% of $Na_2CO_3$, 42.9% of cellulose, 31.8% of $H_2O$ was obtained by immersing wood pulp in 49% aqueous solution of sodium hydroxide and then by pressing it. A reactor was charged with 100 parts by weight of the alkaline cellulose. Then, nitrogen gas replacement was carried out. After the replacement, 5 parts by weight of propylene oxide was charged in the reactor and reacted with stirring at 40° C. for 1 hour, at 50° C. for 1 hour and at 70° C. for 1 hour to provide 103 parts by weight of a reactant.

On the other hand, kneader was charged with 2.5 parts by weight of hot water at 65° C. and 0.13 parts by weight of glacial acetic acid (40% by weight against equivalent for neutralization, initial neutralized acid) and therein, 1 part by weight of the above resulting alkaline cellulose was dispersed. Then, the temperature was adjusted at 30° C. to dissolve a part of the reactant, and 0.20 part by weight of glacial acetic acid (remain of equivalent for neutralization, complete neutralized acid) to provide a processed fiber product containing a part of dissolution and a part of deposit.

The resulting product was washed with hot water at 80° C., drained, dried, ground by means of high rolling impact grinder, and sifted by means of a 100 mesh sieve to provide the powder of low-substituted hydroxypropylcellulose LH-33 (content of hydroxypropoxyl group: 5.8% by weight, average particle diameter: 17.8 μm).

Reference Example 2

Powders of low-substituted hydroxypropylcellulose LH-23, which have a little bigger average particle diameter (content of hydroxypropyl group: 5.7% by weight, average particle diameter: 30.8 µm) were obtained in the same manner as in Reference Example 1.

Example 1

(1) Production of Powders Having a Core

A centrifugal coating granulator [manufactured by Powrex Corp. (Japan), MP-10] was charged with 900 g of Nonpareil 105 (trade name) (particle diameter: 100 to 200 µm). While the inlet air temperature and the outlet air temperature were controlled at 70° C. and 30° C. respectively, the Nonpareil was coated by spraying a spray liquid of the following composition prepared in advance in accordance with the tangential spray method at the spray rate of 22 g/min. Then, drying was carried out for 10 minutes. The resulting granules were sieved through a #60 circular sieve (250 µm) and a #100 circular sieve (150 µm) to provide 2186 g of powders (150 to 250 µm) having a core.

| [Spray liquid] | |
| --- | --- |
| Lansoprazole | 927 g |
| Magnesium carbonate | 309 g |
| Low-substituted hydroxypropylcellulose LH-32 (Content of hydroxypropyl group: 8.8% by weight) (Average particle diameter: 17.57 µm) | 154.5 g |
| Hydroxypropylcellulose (Type SSL) | 309 g |
| Purified water | 3955 g |

(2) Production of Film-Undercoated Powders Having a Core

A centrifugal fluidized coating granulator [manufactured by Powrex Corp. (Japan), MP-10] was charged with 2040 g of the above powders having a core. While the inlet air temperature and the outlet air temperature were controlled at 75° C. and 40° C. respectively, an undercoating liquid of the following composition prepared in advance was sprayed in accordance with the tangential spray method at the spray rate of 13 g/min. 2145 g of film-undercoated powders having a core was obtained.

| [Undercoating liquid] | |
| --- | --- |
| Hydroxypropylmethylcellulose (Type 2910, viscosity: 3 centistokes) | 264 g |
| Purified water | 5016 g |

(3) Production of Enteric-Coated Powders Having a Core

A centrifugal fluidized coating granulator [manufactured by Powrex Corp. (Japan), MP-10] was charged with 1710 g of the above film-undercoated powders having a core. While the inlet air temperature and the outlet air temperature were controlled at 70° C. and 40° C. respectively, an enteric film coating liquid of the following composition prepared in advance was sprayed in accordance with the tangential spray method at the spray rate of 19 g/min. Then, drying was carried out for 7 minutes. The resulting granules were sieved through a #42 circular sieve (355 µm) and a #80 circular sieve (177 µm) to provide 2393 g of powders (177 to 355 µm) having a core.

| [Enteric film coating liquid] | |
| --- | --- |
| Eudragit L30D-55 | 5016.4 g |
| Eudragit NE30D | 559.0 g |
| Triethyl citrate | 333.7 g |
| Glyceryl monostearate | 106.5 g |
| Polysorbate 80 | 34.8 g |
| Red iron oxide | 1.8 g |
| Purified water | 2547.1 g |

(4) Production of Mannitol-Overcoated Enteric-Coated Powders Having a Core

A centrifugal fluidized coating granulator [manufactured by Powrex Corp. (Japan), MP-10] was charged with 600 g of the above enteric-coated powders having a core. While the inlet air temperature and the outlet air temperature were controlled at 65° C. and 32° C. respectively, a film coating liquid of the following composition prepared in advance was sprayed in accordance with the tangential spray method at the spray rate of 11 g/min. Then, drying was carried out for 7 minutes. 617 g of overcoated enteric-coated powders having a core was obtained.

| [Film coating liquid] | |
| --- | --- |
| Mannitol | 33 g |
| Purified water | 297 g |

(5) Production of Mannitol Granulated Powders

A fluidized bed granulator [manufactured by Powrex Corp. (Japan), LAB-1] was charged with 800 g of mannitol [manufactured by Merck Japan Co., Ltd.], and granulation was carried out while spraying 315 g of purified water. The granules were dried to provide 727.3 g of granulated powders.

(6) Production of Mixed Powders

To 105 g of the above overcoated enteric-coated powders having a core were added 97.3 g of the above mannitol-granulated powders, 15.0 g of low-substituted hyroxypropyl cellulose LH-33 (content of hydroxypropoxyl group: 5.8% by weight, average particle diameter: 17.8 µm), 22.5 g of crystalline cellulose [CEOLUS KG-801 (trade name), manufactured by Asahi Chemical Industry Co., Ltd. (Japan)], 7.5 g of crospovidone, 1.5 g of anhydrous citric acid, 0.45 g of aspartane and 0.75 g of magnesium stearate, which were admixed in a bag to give mixed powders.

(7) Production of Orally Disintegrable Tablets 250 g of the above mixed powder was tabletted by a pounder (15R, 11 mm in diameter) using a rotary type tabletting machine at the tabletting pressure of 1.5 ton/cm² to provide tablets each weighting 500 mg.

The hardness and oral disintegration time of each tablet thus obtained were 5.9 kg and 30 seconds respectively.

Example 2

(1) Production of Granules Having a Core

A centrifugal fluidized coating granulator [manufactured by Powrex Corp. (Japan), MP-10 (Type 2)] was charged with 900 g of Nonpareil 105 (trade name) (particle diameter of 100 to 200 µm). With the inlet air temperature and the temperature of the loading being controlled at 65° C. and about 30° C. respectively, the Nonpareil was coated by spraying a bulk liquid of the following composition prepared in advance in accordance with the tangential spray method at a spray rate of 22 g/min. The spraying operation was stopped when the specified amount 5661 g of the bulk liquid had been sprayed, and then drying was carried out in the granulator for 8 minutes. The resulting granules were sieved through a #42 circular sieve (350 μm) and a #100 circular sieve (150 μm) to provide 2074 g of granules having a core.

| Bulk liquid: | |
|---|---|
| Lansoprazole | 1080 g |
| Magnesium carbonate | 360 g |
| Low-substituted hydroxypropyl cellulose LH-32 (hydroxypropoxyl group contents: 8.8 weight %) | 180 g |
| Hydroxypropyl cellulose (Type SSL) | 360 g |
| Purified water | 4680 g |

(2) Production of Film-Undercoated Granules Having a Core

A centrifugal fluidized coating granulator [manufactured by Powrex Corp. (Japan), MP-10 (Type 2)] was charged with 2074 g of the above granules having a core. With the inlet air temperature and the temperature of the loading being controlled at 78° C. and about 40° C., respectively, an undercoating liquid of the following composition prepared in advance was sprayed in accordance with the tangential spray method at a spray rate of 22 g/min. The spraying operation was stopped when the specified amount 1980 g of the undercoating liquid had been sprayed, and then drying was carried out in the granulator for 9 minutes. The resulting granules were sieved through a 190 42 circular sieve (350 μm) and a #100 circular sieve (150 μm) to provide 2555 g of film-undercoated granules having a core.

| Undercoating liquid: | |
|---|---|
| Hydroxypropylmethylcellulose (Type 2910, viscosity: 3 centistokes) | 252 g |
| Titanium oxide (TiO$_2$) | 108 g |
| Sterilized Talc (trade name) [produced by Matsumura Sangyo Co. Ltd. (Japan)] | 108 g |
| Low-substituted hydroxypropyl cellulose LH-32 (hydroxypropoxyl group contents: 8.8 weight %) | 180 g |
| Mannitol | 252 g |
| Purified water | 3600 g |

(3) Production of Enteric Coated Granules Having a Core

A centrifugal fluidized coating granulator [manufactured by Powrex Corp. (Japan), MP-10 (Type 2)] was charged with 1320 g of the above film-undercoated granules having a core. With the inlet air temperature and the temperature of the loading being controlled at 80° C. and about 42° C., respectively, an enteric film coating liquid (A) of the following composition prepared in advance was sprayed in accordance with the tangential spray method at a spray rate of 22 g/min. The specified amount 1638 g of the enteric film coating liquid had been sprayed.

| Enteric film coating liquid (A): | |
|---|---|
| Eudragit L30D-55 | 1219.2 g |
| Eudragit NE30D | 134.4 g |
| Polyethylene glycol 6000 | 40.8 g |
| Glyceryl monostearate | 24.0 g |
| Polysorbate 80 | 7.2 g |
| Ferric oxide | 0.24 g |
| Ferric oxide (yellow) | 0.24 g |
| Citric acid anhydrous | 0.48 g |
| Purified water | 1693 g |

Following this, with the inlet air temperature and the temperature of the loading being controlled at 76° C. and about 42° C., respectively, an enteric film coating liquid (B) of the following composition prepared in advance was sprayed in accordance with the tangential spray method at a spray rate of 22 g/min. The specified amount 6552 g of the enteric film coating liquid had been sprayed.

| Enteric film coating liquid (B): | |
|---|---|
| Eudragit L30D-55 | 4032 g |
| Eudragit NE30D | 447.8 g |
| Triethyl citrate | 269.3 g |
| Glyceryl monostearate | 86.4 g |
| Polysorbate 80 | 25.9 g |
| Ferric oxide | 0.86 g |
| Ferric oxide (yellow) | 0.86 g |
| Citric acid anhydrous | 0.72 g |
| Purified water | 2624 g |

Following this, with the inlet air temperature and the temperature of the loading being controlled at 80° C. and about 42° C., respectively, an enteric film coating liquid (A) of the above mentioned composition prepared in advance was sprayed in accordance with the tangential spray method at a spray rate of 22 g/min. The specified amount 819 g of the enteric film coating liquid had been sprayed.

(4) Production of Enteric Coated and Mannitol Coated Granules Having a Core

Following (3), with the inlet air temperature and the temperature of the loading being controlled at 85° C. and about 35° C., respectively, an film coating liquid of the following composition prepared in advance was sprayed in accordance with the tangential spray method at a spray rate of 22 g/min. using a centrifugal fluidized coating granulator [manufactured by Powrex Corp. (Japan), MP-10 (Type 2)]. The spraying operation was stopped when the specified amount 882 g of the film coating liquid had been sprayed, and then drying was carried out in the granulator for 10 minutes. The resulting granules were sieved through a #35 circular sieve (420 μm) and a #60 circular sieve (250 μm) to provide 1964 g of enteric coated and mannitol coated granules having a core.

The average particle diameter of the obtained granules was 333.7 μm.

| Film coating liquid: | |
|---|---|
| Mannitol | 180 g |
| Purified water | 1080 g |

(5) Production of Mixed Powders

To 270 g of the above enteric coated and mannitol coated granules having a core were added 204.0 g of mannitol, 30 g of low-substituted hydroxypropyl cellulose LH-33 (hydroxypropoxyl group contents: 5.8 weight %), 30 g of crystalline cellulose [CEOLUS KG-801 (trade name), manufactured by Asahi Chemical Co., Ltd. (Japan)], 15 g of crospovidone, 3 g of citric acid anhydrous, 9 g of aspartame, 6 g of magnesium stearate and 3 g of flavor [STRAWBERRY DURAROME (trade name), manufactured by Nihon Filmenich Co., Ltd. (Japan)], which was admixed in a bag to give mixed powders.

(6) Production of Orally Disintegrable Tablets 570 g of the above mixed powders were tabletted using Autograph (trade name; compressing force measurement apparatus) with a punch having a beveled edge, 13 mm in diameter, at a tableting pressure of 1.5 ton/cm$^2$, to provide tablets each weighting 570 mg.

The hardness and oral disintegration time of each tablet thus obtained were 2.6 kg and 20 seconds, respectively.

The acid-resistance of the obtained tablet was 3.5%

Example 3

A fluidized bed granulator [manufactured by Powrex Corp. (Japan), LAB-1] was charged with 0.6 g of voglibose, 410.4 g of erythritol [manufactured by Nikken Chemicals, Co., Ltd. (Japan)], 120.0 g of low-substituted hydroxypropylcellulose LH-33 (content of hydroxypropoxyl group: 5.8% by weight, average particle diameter: 17.8 μm), 30.0 g of CEOLUS KG-801 [manufactured by Asahi Chemical Industry Co., Ltd. (Japan)], 30 g of crospovidone, 6.0 g of anhydrous citric acid and 1.2 g of aspartame, and granulation was carried out while spraying purified water. After drying, 1.8 g of magnesium stearate was incorporated. The resulting powder was tabletted by a pounder (beveled edge, 10 mm in diameter) using a rotary type tabletting machine at the tabletting pressure of 1.0 ton/cm$^2$ to provide tablets each weighting 300 mg.

The hardness and oral disintegration time of each tablet thus obtained were 10.7 kg and 26 seconds respectively.

Example 4

A fluidized bed granulator [manufactured by Powrex Corp. (Japan), LAB-1] was charged with 0.6 g of voglibose, 440.4 g of erythritol [manufactured by Nikken Chemicals, Co., Ltd. (Japan)], 120.0 g of low-substituted hydroxypropylcellulose LH-33 (content of hydroxypropoxyl group: 5.8% by weight, average particle diameter: 17.8 μm), 30.0 g of crospovidone, 6.0 g of anhydrous citric acid and 1.2 g of aspartame, and granulation was carried out while spraying purified water. After drying, 1.8 g of magnesium stearate was incorporated. The resulting powder was tabletted by a pounder (beveled edge, 10 mm in diameter) using a rotary type tabletting machine at the tabletting pressure of 1.0 ton/cm$^2$ to provide tablets each weighting 300 mg.

The hardness and oral disintegration time of each tablet thus obtained were 7.1 kg and 20 seconds respectively.

Example 5

A fluidized bed granulator [manufactured by Powrex Corp. (Japan), LAB-1] was charged with 0.4 g of voglibose, 470.6 g of erythritol [manufactured by Nikken Chemicals Co., Ltd. (Japan)], 120.0 g of low-substituted hydroxypropylcellulose LH-33 (content of hydroxypropoxyl group: 5.7% by weight, average particle diameter: 30.8 μm), 6.0 g of anhydrous citric acid and 1.2 g of aspartame, and granulation was carried out while spraying purified water. After drying, 1.8 g of magnesium stearate was incorporated. The resulting powders was tabletted by a pounder (beveled edge, 10 mm in diameter) using a rotary type tabletting machine at the tabletting pressure of 1.25 ton/cm$^2$ to provide tablets each weighting 300 mg.

The hardness and oral disintegration time of each tablet thus obtained were 4.5 kg and 23 seconds respectively.

Example 6

A fluidized bed granulator [manufactured by Powrex Corp. (Japan), LAB-1] was charged with 0.4 g of voglibose, 470.6 g of mannitol [manufactured by Merck Japan Co., Ltd.], 120.0 g of low-substituted hydroxypropylcellulose LH-23 (content of hydroxypropoxyl group: 5.7% by weight, average particle diameter: 30.8 μm), 6.0 g of anhydrous citirc acid and 1.2 g of aspartame, and granulation was carried out while spraying purified water. After drying, 1.8 g of magnesium stearate was incorporated. The resulting powder was tabletted by a pounder (beveled edge, 10 mm in diameter) using a rotary type tabletting machine at the tabletting pressure of 1.25 ton/cm$^2$ to provide tablets each weighting 300 mg.

The hardness and oral disintegration time of each tablet thus obtained were 4.3 kg and 27 seconds respectively.

Example 7

A fluidized bed granulator [manufactured by Powrex Corp. (Japan), LAB-1] was charged with 40.0 g of manidipine hydrochloride, 460.94 g of erythritol [manufactured by Nikken Chemicals Co., Ltd. (Japan)], 60.0 g of low-substituted hydroxypropylcellulose LH-33 (content of hydroxypropoxyl group: 5.8% by weight, average particle diameter: 17.8 μm), 30.0 g of crospovidone, 6.0 g of anhydrous citric acid and 1.2 g of aspartame, and granulation was carried out while spraying purified water in which was dissolved 0.06 of yellow iron oxide. After drying, 1.8 g of magnesium stearate was incorporated. The resulting powder was tabletted by a pounder (beveled edge, 10 mm in diameter) using a rotary type tabletting machine at the tabletting pressure of 1.0 ton/cm$^2$ to provide tablets each weighting 300 mg.

The hardness and oral disintegration time of each tablet thus obtained were 6.0 kg and 21 seconds respectively.

Test Example 1

Low-substituted hydroxypropylcellulose LH-30 (content of hydroxypropoxyl group: 14.6% by weight, average particle diameter: 17.26 μm), LH-31 (content of hydroxypropoxyl group: 11.0% by weight, average particle diameter: 18.18 μm), LH-32 (content of hydroxypropoxyl group: 8.8% by weight, average particle diameter: 17.57 μm) and LH-33 (content of hydroxypropoxyl group: 5.8% by weight, average particle diameter: 17.8 μm) were administered to 4 females respectively, and dissolubility and taste were evaluated.

The results are shown in [Table 1].

TABLE 1

| Low-substituted hydroxypropylcellulose | Trial subject | Evaluation |
| --- | --- | --- |
| LH-30 | 4/4 | difficult of dissolution in the oral cavity |
| LH-31 | 4/4 | dissolved in the oral cavity, chalky taste |
| LH-32 | 4/4 | dissolved in the oral cavity, chalky taste |
| LH-33 | 4/4 | dissolved in the oral cavity, no chalky taste |

As shown in [Table 1], dissolubility and chalky taste are improved, and further no roughness was felt, with respect to the case of low-substituted hydroxypropylcellulose LH-33 comprising 5.8% by weight of hydroxypropoxyl group.

Test Example 2

Tablets were produced by using low-substituted hydroxypropylcellulose LH-30 (content of hydroxypropoxyl group: 14.6% by weight, average particle diameter: 17.26 μm), LH-31 (content of hydroxypropoxyl group: 11.0% by weight, average particle diameter: 18.18 μm), LH-32 (content of hydroxypropoxyl group: 8.8% by weight, average particle diameter: 17.57 μm) and LH-33 (content of hydroxypropoxyl group: 5.8% by weight, average particle diameter: 17.8 μm) in accordance with the following manner.

A fluidized bed granulator [manufactured by Powrex Corp. (Japan), LAB-1] was charged with 398.5 g of erythritol [manufactured by Nikken Chemicals Co., Ltd. (Japan)] and 100 g of low-substituted hydroxypropylcellulose, and granulation was carried out while spraying purified water. After drying, 1.5 g of magnesium stearate was incorporated. The resulting power was tabletted by a pounder (beveled edge, 10 mm in diameter) using a rotary type tabletting machine at the tabletting pressure of 1.0 ton/cm$^2$ to provide tablets each weighting 300 mg.

The resulting tablets were administered to 4 females respectively, and dissolubility and taste was evaluated.

TABLE 2

| Low-substituted hydroxypropylcellulose | Trial subject | Evaluation |
| --- | --- | --- |
| LH-30 | 4/4 | not dissolved in the oral cavity |
| LH-31 | 4/4 | not dissolved in the oral cavity |
| LH-32 | 4/4 | felt adhesiveness in the oral cavity, still chalky taste after dissolution |
| LH-33 | 4/4 | rapidly dissolved in the oral cavity, a little chalky taste |

As shown in [Table 2], dissolubility and chalky taste are improved, and further no roughness was felt, with respect to the case of low-substituted hydroxypropylcellulose LH-33 comprising 5.8% by weight of hydroxypropoxyl group.

EFFECTS OF INVENTION

The rapidly disintegrable solid preparation of the present invention is usable for treatment and prevention of various kinds of diseases especially as the oral rapidly disintegrable solid preparation, which is capable of being administered to elders or children without water, because the preparation has superior disintegrability and dissolubility. It is also improved in its disintegrability in the stomach.

And, the rapidly disintegrable solid preparation has superior long-term stability because the preparation has suitable strength.

Further, the rapidly disintegrable solid preparation of the present invention is improved in dissolubility and chalky taste, and has no roughness.

The invention claimed is:

1. An oral rapidly disintegrable solid preparation which comprises (i) manidipine hydrochloride, (ii) a sugar and (iii) a low-substituted hydroxypropylcellulose having 5% by weight or more to less than 7% by weight of hydroxypropoxyl groups; wherein said solid preparation is buccally dissolved in from about 5 to about 50 seconds.

2. An oral rapidly disintegrable solid preparation which comprises (i) pioglitazone hydrochloride, (ii) a sugar and (iii) a low-substituted hydroxypropylcellulose having 5% by weight or more to less than 7% by weight of hydroxypropoxyl groups; wherein said solid preparation is buccally dissolved in from about 5 to about 50 seconds.

* * * * *